(12) United States Patent
Burgazli et al.

(10) Patent No.: US 11,261,389 B2
(45) Date of Patent: Mar. 1, 2022

(54) COMPOSITIONS AND METHODS AND USES RELATING THERETO

(71) Applicants: Cenk R. Burgazli, Middletown, DE (US); Christopher E. LeMieux, Dover, DE (US)

(72) Inventors: Cenk R. Burgazli, Middletown, DE (US); Christopher E. LeMieux, Dover, DE (US)

(73) Assignee: Innospec Limited, Ellesmere Port (GB)

(*) Notice: Subject to any disclaimer, the term of this patent is extended or adjusted under 35 U.S.C. 154(b) by 0 days.

(21) Appl. No.: 16/875,365

(22) Filed: May 15, 2020

(65) Prior Publication Data
US 2020/0362255 A1 Nov. 19, 2020

Related U.S. Application Data

(60) Provisional application No. 62/848,311, filed on May 15, 2019.

(30) Foreign Application Priority Data

Jun. 21, 2019 (GB) .................................... 1908912

(51) Int. Cl.
| | | |
|---|---|---|
| C10L 1/00 | (2006.01) | |
| C07C 309/38 | (2006.01) | |
| C10L 1/24 | (2006.01) | |
| C09K 11/06 | (2006.01) | |
| G01N 21/64 | (2006.01) | |
| G01N 33/28 | (2006.01) | |

(52) U.S. Cl.
CPC ............ *C10L 1/003* (2013.01); *C07C 309/38* (2013.01); *C09K 11/06* (2013.01); *C10L 1/2437* (2013.01); *G01N 21/64* (2013.01); *G01N 33/2882* (2013.01); *C07C 2603/50* (2017.05); *C09K 2211/1011* (2013.01); *C10L 2200/0263* (2013.01); *C10L 2200/0423* (2013.01); *C10L 2200/0446* (2013.01); *C10L 2230/18* (2013.01)

(58) Field of Classification Search
CPC . C07C 211/63; C07C 2603/50; C07C 309/33; C07C 309/38; C09K 11/06; C09K 2211/1011; C10L 1/003; C10L 1/2222; C10L 1/2437; C10L 2200/0263; C10L 2200/0423; C10L 2200/0446; C10L 2230/16; C10L 2230/18; G01N 21/64; G01N 33/2882
See application file for complete search history.

(56) References Cited

U.S. PATENT DOCUMENTS

| | | | |
|---|---|---|---|
| 2,482,760 A | 9/1949 | Goebel | |
| 2,482,761 A | 9/1949 | Goebel | |
| 2,731,481 A | 1/1956 | Harrison et al. | |
| 2,764,548 A | 9/1956 | King et al. | |
| 2,793,219 A | 5/1957 | Barrett et al. | |
| 2,964,545 A | 12/1960 | Harrison | |
| 2,978,468 A | 4/1961 | Hampton | |
| 3,157,681 A | 11/1964 | Fischer | |
| 3,256,304 A | 6/1966 | Fischer et al. | |
| 4,931,588 A † | 6/1990 | Kawagishi | |
| 5,164,179 A † | 11/1992 | Hioki | |
| 5,187,214 A † | 2/1993 | Govindan | |
| 5,672,182 A † | 9/1997 | Smith | |
| 5,753,600 A * | 5/1998 | Kamegai | A61K 8/4926 510/119 |
| 5,863,909 A † | 1/1999 | Kurita | |
| 9,060,514 B2 † | 6/2015 | Yamaguchi | |
| 2005/0260764 A1* | 11/2005 | Grigsby, Jr. | G01N 21/6428 436/172 |
| 2009/0319195 A1 | 12/2009 | Hoots et al. | |
| 2010/0067958 A1 | 3/2010 | Kishida et al. | |
| 2014/0238328 A1* | 8/2014 | Fang | C10L 1/2222 123/1 A |

FOREIGN PATENT DOCUMENTS

| | | |
|---|---|---|
| CN | 107460012 A | 12/2017 |
| CN | 108373922 A | 8/2018 |

(Continued)

OTHER PUBLICATIONS

K. Ertekin et al., "Characterization of a reservoir-type capillary optical microsensor for pCO2 measurements," Talanta 59 (2003) 261-267.
O. S. Wolfbeis et al., "Fiber-Optic Fluorescence Carbon Dioxide Sensor for Environmental Monitoring," Mikrochim. Acta 129, 181-188 (1998).

(Continued)

*Primary Examiner* — Ellen M McAvoy
*Assistant Examiner* — Chantel L Graham
(74) *Attorney, Agent, or Firm* — Burns & Levinson LLP; Janine M. Susan (57) ABSTRACT

A compound of formula (I):

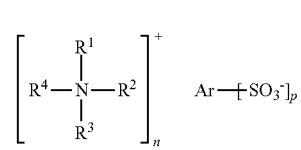

wherein p is at least 1, n is at least 1 and less than or equal to p; Ar is a polycyclic aromatic moiety, $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms.

21 Claims, 2 Drawing Sheets

(56) References Cited

FOREIGN PATENT DOCUMENTS

| JP | H04215830 A † | 8/1992 |
|---|---|---|
| JP | 2011065977 A | 3/2011 |
| JP | 2016047892 A | 4/2016 |
| PL | 215438 B1 | 7/2011 |
| WO | 1996022344 A1 | 7/1996 |
| WO | WO 2004029017 A1 † | 4/2004 |
| WO | 2005064336 A1 | 7/2005 |
| WO | 2012055481 A1 | 5/2012 |
| WO | 2016016641 A1 | 2/2016 |

OTHER PUBLICATIONS

Combined Search and Examination Report issued in GB2006922.5, dated Oct. 28, 2020.
International Search Report and Written Opinion issued in PCT/GB2020/051145, dated Aug. 13, 2020.
Search Report issued in GB Application No. 1908912.7 dated Dec. 6, 2019.
H. Sutterlin; Mixtures of quaternary ammonium compounds and ionic organic compounds in the aquatic environment: Elimination and biodegradability in the closed bottle test monitored by LC-MS/MS; pp. 479-484; published 2008; published by Elsevier Ltd.; published in Chemosphere 72 (2008) 479-484.†
Maria Angela Castriciano; Novel Luminescent Ionic Adducts Based on Pyrene-1-sulfonate; pp. 18811-18820; published 2018; published by the American Chemical Society; ACS Omega 2018, 3, 18811-18820.†

\* cited by examiner
† cited by third party

COMPOSITIONS AND METHODS AND USES RELATING THERETO

CROSS-REFERENCE TO RELATED APPLICATIONS

This application claims benefit of and priority to U.S. Provisional Application No. 62/848,311, filed May 15, 2019, entitled COMPOSITIONS AND METHODS AND USES RELATING THERETO, and also claims priority to and the benefit of Great Britain Application No. 1908912.7, filed Jun. 21, 2019, the contents of which are incorporated by reference herein in their entirety for all purposes.

FIELD

The present invention relates to novel marker compounds, to methods of preparing such compounds and to uses of said compounds.

In particular the invention relates to the use of marker compounds in fuel additive compositions, especially those containing corrosion inhibitors.

BACKGROUND

Additives are used in all types of fuels for a wide variety of purposes. They are included in, for example, gasoline fuels and middle distillate fuels, for example diesel. They are also used in blends of mineral or synthetic fuels and biofuels, for example blends of gasoline and ethanol or blends of biodiesel and mineral diesel.

Additives are incorporated into fuel compositions for a number of reasons. For example they may be included to improve performance properties of the fuel, for example the low temperature or combustion properties; they may be included to protect infrastructure used during storage and handling of the fuels, to reduce damage to engines or other surfaces that fuels come into contact with, or they may be included for environmental reasons, to reduce harmful emissions.

Common classes of additives dosed into fuel include detergents, dispersants, antioxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, static dissipator additives, combustion improvers, wax anti-settling agents, cold flow improvers, cetane improvers, dyes, other markers and drag reducers.

Additives of the above classes will be well known to the skilled person working in the field of the present invention.

The effectiveness of any additive depends on the treat rate at which it is added and optimum treat rates may vary from fuel to fuel.

Fuels are complex mixtures of compounds and most fuels used in engines also contain a number of different additives. It is therefore difficult to determine the level of a particular additive present in any formulated fuel. However it is important to be able to determine whether additives have been dosed into fuels in the correct amounts. If the dose used is too low, then the desired effect may not be achieved. In the case of corrosion inhibitors, for example, insufficient dose levels can lead to corrosion of equipment which can result in fuel leakage and environmental pollution, or cause severe damage to equipment that can be dangerous and extremely costly to equipment operators. Too high doses can also cause problems. As well as the unnecessary expense, some additives can cause deposits on combustion and thus should be included at the minimum concentration needed to achieve a desired effect.

It is therefore extremely useful to be able to determine whether the correct amount of an additive or an additive composition has been dosed into a particular formulated fuel.

One way in which it is possible to measure the concentration of an additive is to include in an additive composition a marker compound whose concentration can be determined, for example by spectroscopic means. It is known to add certain fluorescent compounds to additive compositions for such purposes. The use of Rhodamine compounds is described, for example, in US2009/0319195.

Fluorescent markers are generally known. However the selection of a suitable marker for inclusion in a fuel composition is not a simple undertaking as there are a number of considerations to take into account. It is generally undesirable to include coloured markers since the resulting fuels may be confused with fuels to which dyes are deliberately added to indicate their use for off-road purposes (e.g. red dyed diesel).

The use of markers including metallic species is also highly undesirable in fuels as their combustion may lead to increased deposits.

In addition, the solubility of any marker in a fuel or an additive concentrate composition comprising various components must be considered, as well as the potential interaction of the marker with other additives and/or other markers that may be present.

For the above reasons, and because fuels may comprise a number of additives, there is a continuing need to develop marker compounds for inclusion in fuel additive compositions.

SUMMARY

The present invention provides a class of novel marker compounds having advantageous properties that are suitable for use in fuel additive compositions.

According to some aspects of the present invention, there is provided a compound of formula (I):

p is at least 1, n is at least 1 and less than or equal to p. Ar is a polycyclic aromatic moiety. $R^1$ is hydrogen or an optionally substituted hydrocarbyl group. Each of $R^2$, $R^3$ and $R^4$ is independently an optionally substituted hydrocarbyl group, provided that at least one of $R^2$, $R^3$ and $R^4$ has at least 6 carbon atoms.

According to other aspects of the present invention, there is provided a method of preparing a compound of formula (I):

The method includes admixing (a) a quaternary ammonium salt, a tertiary amine or a tertiary amine salt with (b) a sulfonated polycyclic aromatic compound. In some embodiments, component (a) includes a quaternary ammonium salt or a tertiary amine salt, and the method involves admixing a compound of formula (III):

and compound of formula (IV):

Ar is a polycyclic aromatic moiety. p is at least 1. $X^+$ is a proton, an ammonium ion or a metal ion. $R^1$ is hydrogen or an optionally substituted hydrocarbyl group. Each of $R^2$, $R^3$ and $R^4$ is independently an optionally substituted hydrocarbyl group, provided that at least one of $R^2$, $R^3$ and $R^4$ has at least 6 carbon atoms. $Y^-$ is an anion.

According to other aspects of the present invention, there is provided a composition including a compound of formula (I):

p is at least 1. n is at least one and is less than or equal to p. Ar is a polycyclic aromatic moiety. $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms. In some embodiments, the composition is an additive composition for a fuel and further includes one or more fuel additives.

According to other aspects of the present invention, there is provided a fuel composition including a fuel, one or more additives and a compound of formula (I):

p is at least 1. n is at least 1 and is less than or equal to p. Ar is a polycyclic aromatic moiety. $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms. In some embodiments, the fuel includes gasoline, ethanol or mixtures thereof. In other embodiments, the fuel is diesel.

According to other aspects of the present invention, there is provided a method of preparing a fuel composition including preparing an additive composition as described above and dosing the additive composition into a fuel. In some embodiments, the method also includes preparing the additive composition, dosing the additive composition into an ethanol component of a fuel composition, and blending the ethanol component with a gasoline fuel.

According to other aspects of the present invention, there is provided a use of a compound of formula (I):

as a fluorescent marker. p is at least 1. n is at least 1 and is less than or equal to p. Ar is a polycyclic aromatic moiety. $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms.

According to other aspects of the present invention, there is provided a method of determining the presence of an additive in a fuel composition including an additive and a compound of formula (I). The method includes applying electromagnetic radiation having a first wavelength to the fuel composition and determining the emission of electromagnetic radiation from the compound of formula (I) at a second wavelength.

According to other aspects of the present invention, there is provided a method of determining the concentration of a first additive in a fuel composition including a first additive and a compound of formula (I). The compound of formula (I) is present in the fuel composition at a concentration that is proportional to the concentration of the first additive. The method includes applying electromagnetic radiation having a first wavelength to the fuel composition, measuring emission of electromagnetic radiation from the compound of formula (I) at a second wavelength, and calculating from the level of emission at the second wavelength the concentration of the first additive in the fuel composition.

According to other aspects of the present invention, there is provided a method of determining the concentration of an additive composition that has been dosed into a fuel composition. The additive composition includes a compound of formula (I) and at least one further additive. The method includes applying electromagnetic radiation having a first wavelength to the fuel composition, measuring emission of electromagnetic radiation from the compound of formula (I) at a second wavelength, and calculating from the level of emission at the second wavelength the concentration of the compound of formula (I) in the fuel composition.

In some embodiments of the composition, method or use, $R^1$ is hydrogen or an alkyl, alkenyl or alkaryl group having 1 to 12 carbon atoms and each of $R^2$, $R^3$ and $R^4$ is an alkyl, alkenyl or alkaryl group having 1 to 36 carbon atoms, provided that that at least one of $R^2$, $R^3$ and $R^4$ has at least 6 carbon atoms.

In some embodiments of the composition, method or use, $R^1$ is hydrogen or an alkyl group having 1 to 4 carbon atoms, $R^2$ is benzyl or an alkyl group having 1 to 4 carbon atoms, and each of $R^3$ and $R^4$ is an alkyl, alkenyl or alkaryl group having 1 to 36 carbon atoms, provided that that at least one of $R^3$ and $R^4$ has at least 6 carbon atoms.

In some embodiments of the composition, method or use, $R^1$, $R^2$, $R^3$ and $R^4$ together comprise in total from 16 to 40 carbon atoms, preferably from 20 to 36 carbon atoms, for example from 20 to 30 carbon atoms.

In some embodiments of the composition, method or use, $R^1$, $R^2$, $R^3$ and $R^4$ is an unsubstituted alkyl or alkenyl group, and each of $R^3$ and $R^4$ has at least 6 carbon atoms.

In some embodiments of the composition, method or use, $R^1$ is hydrogen or an unsubstituted alkyl group having 1 to 4 carbon atoms. $R^2$ is an unsubstituted alkyl group having 1 to 4 carbon atoms or an unsubstituted alkyl or alkenyl group having 6 to 36 carbon atoms, preferably 8 to 30 carbon atoms. $R^3$ is benzyl, an unsubstituted alkyl group having 1 to 4 carbon atoms or an unsubstituted alkyl or alkenyl group having 6 to 36 carbon atoms, preferably 8 to 30 carbon atoms. $R^4$ is an unsubstituted alkyl or alkenyl group having 6 to 36 carbon atoms, preferably 8 to 30 carbon atoms.

In some embodiments of the composition, method or use, n is from 1 to 4.

In some embodiments of the composition, method or use, Ar is based on a fluorene, naphthalene, anthracene or pyrene moiety, or an isomer thereof.

In some embodiments of the composition, method or use, the compound of formula (I) has the structure (II):

(II)

or an isomer thereof.

According to other aspects of the present invention, there is provided a kit for determining the concentration of a compound of formula (I) in a fuel composition. The kit includes means for applying electromagnetic radiation having a first wavelength to the fuel composition, and means for measuring emission of electromagnetic radiation at a second wavelength.

DETAILED DESCRIPTION

According to a first aspect of the present invention there is provided a compound of formula (I):

(I)

wherein p is at least 1, n is at least 1 and less than or equal to p, Ar is a polycyclic aromatic moiety, $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms.

p is at least 1 and n is at least 1 and less than or equal to p. The skilled person will appreciate that n may be less than p in embodiments in which insufficient ammonium ions are present to neutralise all of the sulfonic acid residues. In preferred embodiments n=p.

$R^1$ is hydrogen or an optionally substituted hydrocarbyl group. Preferably $R^1$ is hydrogen or an an optionally substituted alkyl, alkenyl, aryl, aralkyl or alkaryl group. More preferably $R^1$ is hydrogen or an optionally substituted alkyl, alkenyl or alkaryl group. Most preferably $R^1$ is hydrogen or an unsubstituted alkyl, alkenyl or alkaryl group.

Each of $R^2$, $R^3$ and $R^4$ is independently an optionally substituted hydrocarbyl group. Preferably each of $R^2$, $R^3$ and $R^4$ is independently an optionally substituted alkyl, alkenyl, aryl, aralkyl or alkaryl group.

In some embodiments two or three of $R^2$, $R^3$ and $R^4$ may join together to form a heterocyclic ring. Such heterocyclic rings may be aliphatic or aromatic in nature. Suitable aromatic heterocyclic groups including those based on pyrrole, pyridine, imidazole, pyrimidine, isoxzole, quinolone, oxazole, and pyrazole. Suitable aliphatic heterocyclic groups include those based on pyrrolidine, piperidine, morpholine and piperazine.

Preferably each of $R^2$, $R^3$ and $R^4$ is independently an optionally substituted alkyl, alkenyl or alkaryl group. Most preferably each of $R^2$, $R^3$ and $R^4$ is independently an unsubstituted alkyl, alkenyl or alkaryl group.

Preferably $R^1$ is hydrogen or an alkyl, alkenyl or alkaryl group, preferably an unsubstituted alkyl, alkenyl or alkaryl group; and each of $R^2$, $R^3$ and $R^4$ is an alkyl, alkenyl or alkaryl group, preferably an unsubstituted alkyl, alkenyl or alkaryl group.

Preferably $R^1$ is hydrogen or an alkyl, alkenyl or alkaryl group having 1 to 36 carbon atoms and each of $R^2$, $R^3$ and $R^4$ is an alkyl, alkenyl or alkaryl group having 1 to 36 carbon atoms, provided that that at least one of $R^2$, $R^3$ and $R^4$ has at least 6 carbon atoms. Unsubstituted alkyl, alkenyl or alkaryl groups are especially preferred.

In some embodiments $R^1$ is hydrogen or an alkyl, alkenyl or alkaryl group having 1 to 12 carbon atoms and each of $R^2$, $R^3$ and $R^4$ is an alkyl, alkenyl or alkaryl group having 1 to 36 carbon atoms, provided that that at least one of $R^2$, $R^3$ and $R^4$ has at least 6 carbon atoms. Unsubstituted alkyl, alkenyl or alkaryl groups are especially preferred.

In some embodiments $R^1$ is hydrogen or an alkyl, alkenyl or alkaryl group having 1 to 12 carbon atoms, $R^2$ is an alkyl, alkenyl or alkaryl group having 1 to 12 carbon atoms and each of $R^3$ and $R^4$ is an alkyl, alkenyl or alkaryl group having 1 to 36 carbon atoms, provided that that at least one of $R^3$ and $R^4$ has at least 6 carbon atoms. Unsubstituted alkyl, alkenyl or alkaryl groups are especially preferred.

When $R^1$, $R^2$, $R^3$ or $R^4$ is alkyl or alkenyl, each may be straight chain or branched.

Each of $R^1$, $R^2$, $R^3$ and $R^4$ may comprise a mixture of alkyl or alkenyl groups. This may be the case, for example, when these materials are derived from natural sources. The definitions provided herein should be construed to include such mixtures.

Suitable natural sources from which $R^1$, $R^2$, $R^3$ and $R^4$ may be derived include coconut, tallow, soy, rapeseed, canola, palm and palm kernel.

Each of $R^1$, $R^2$, $R^3$ and $R^4$ may independently comprise a mixture of homologues and/or a mixture of isomers.

In some embodiments one or more of $R^1$, $R^2$, $R^3$ or $R^4$ may be alkaryl. Benzyl is a preferred alkaryl group.

In some embodiments $R^1$ is hydrogen, benzyl or an alkyl or alkenyl group having 1 to 6 carbon atoms and each of $R^2$, $R^3$ and $R^4$ is benzyl or an alkyl or alkenyl group having 1 to 36 carbon atoms, provided that that at least one of $R^2$, $R^3$ and $R^4$ has at least 6 carbon atoms. Unsubstituted alkyl and alkenyl groups are especially preferred.

In some embodiments one of $R^2$, $R^3$ and $R^4$ has at least 6 carbon atoms.

In some embodiments two of $R^2$, $R^3$ and $R^4$ have at least 6 carbon atoms.

In some embodiments three of $R^2$, $R^3$ and $R^4$ have at least 6 carbon atoms.

In some embodiments $R^1$ is hydrogen or an alkyl group having 1 to 4 carbon atoms and each of $R^2$, $R^3$ and $R^4$ is an alkyl, alkenyl or alkaryl group having 1 to 36 carbon atoms, provided that that at least one of $R^2$, $R^3$ and $R^4$ has at least 6 carbon atoms. Unsubstituted alkyl, alkenyl or alkaryl groups are especially preferred.

In some embodiments $R^1$ is hydrogen and each of $R^2$, $R^3$ and $R^4$ is an alkyl, alkenyl or alkaryl group having 1 to 36 carbon atoms, provided that that at least one of $R^2$, $R^3$ and $R^4$ has at least 6 carbon atoms. Unsubstituted alkyl, alkenyl or alkaryl groups are especially preferred.

In some embodiments $R^1$ is hydrogen or an alkyl group having 1 to 4 carbon atoms, $R^2$ is benzyl or an alkyl group having 1 to 4 carbon atoms, and each of $R^3$ and $R^4$ is an alkyl, alkenyl or alkaryl group having 1 to 36 carbon atoms, provided that that at least one of $R^3$ and $R^4$ has at least 6 carbon atoms. Unsubstituted alkyl, alkenyl or alkaryl groups are especially preferred.

In some embodiments $R^1$ is hydrogen or an alkyl group having 1 to 4 carbon atoms, $R^2$ is benzyl or an alkyl group having 1 to 4 carbon atoms, $R^3$ is benzyl or an alkyl group having 1 to 4 carbon atoms, and $R^4$ is an alkyl, alkenyl or alkaryl group having 6 to 36 carbon atoms. Unsubstituted alkyl, alkenyl or alkaryl groups are especially preferred.

In some embodiments $R^1$ is an alkyl group having 1 to 4 carbon atoms, $R^2$ is benzyl or an alkyl group having 1 to 4 carbon atoms, $R^3$ is benzyl or an alkyl group having 1 to 4 carbon atoms, and $R^4$ is an alkyl, alkenyl or alkaryl group having 6 to 36 carbon atoms. Unsubstituted alkyl, alkenyl or alkaryl groups are especially preferred.

In some embodiments $R^1$ is an alkyl group having 1 to 4 carbon atoms, preferably methyl; $R^2$ is an alkyl group having 1 to 4 carbon atoms, preferably methyl; $R^3$ is benzyl or an alkyl group having 1 to 4 carbon atoms, preferably benzyl or methyl; and $R^4$ is an alkyl or alkenyl having 6 to 36 carbon atoms, preferably 10 to 30 carbon atoms. Unsubstituted alkyl and alkenyl groups are especially preferred.

In one embodiment $R^1$ is an alkyl group having 1 to 4 carbon atoms, preferably methyl; $R^2$ is an alkyl group having 1 to 4 carbon atoms, preferably methyl; $R^3$ is an alkyl group having 1 to 4 carbon atoms, preferably methyl; and $R^4$ is an alkyl or alkenyl having 10 to 36 carbon atoms, preferably 20 to 30 carbon atoms. Unsubstituted alkyl and alkenyl groups are especially preferred.

In one embodiment $R^1$ is an alkyl group having 1 to 4 carbon atoms, preferably methyl; $R^2$ is an alkyl group having 1 to 4 carbon atoms, preferably methyl; $R^3$ is benzyl or an alkyl group having 1 to 6 carbon atoms, preferably benzyl; and $R^4$ is an alkyl or alkenyl having 6 to 36 carbon atoms, preferably 20 to 30 carbon atoms. Unsubstituted alkyl and alkenyl groups are especially preferred.

In some preferred embodiments at least two of $R^1$, $R^2$, $R^3$ and $R^4$ have at least 6 carbon atoms.

In some embodiments each of $R^1$ and $R^2$ have less than 6 carbon atoms and $R^3$ and $R^4$ each have at least 6 carbon atoms.

In some embodiments $R^1$ is hydrogen or an alkyl group having 1 to 4 carbon atoms, $R^2$ is an alkyl group having 1 to 4 carbon atoms, and each of $R^3$ and $R^4$ is an alkyl, alkenyl or alkaryl group having 6 to 36 carbon atoms. Unsubstituted alkyl, alkenyl or alkaryl groups are especially preferred.

In some embodiments $R^1$ is hydrogen or an alkyl group having 1 to 4 carbon atoms, $R^2$ is an alkyl group having 1 to 4 carbon atoms, and each of $R^3$ and $R^4$ is an alkyl or alkenyl group having 6 to 36 carbon atoms. Unsubstituted alkyl and alkenyl groups are especially preferred.

In some preferred embodiments $R^1$ is an alkyl group having 1 to 4 carbon atoms, preferably methyl; $R^2$ is an alkyl group having 1 to 4 carbon atoms, preferably methyl; and each of $R^3$ and $R^4$ is an alkyl or alkenyl group having 6 to 36 carbon atoms, preferably 8 to 30 carbon atoms, more preferably 8 to 20 carbon atoms. Unsubstituted alkyl and alkenyl groups are especially preferred.

In some embodiments $R^1$ has less than 6 carbon atoms and $R^2$, $R^3$ and $R^4$ each have at least 6 carbon atoms.

In some embodiments $R^1$ is hydrogen or an alkyl group having 1 to 4 carbon atoms and each of $R^2$, $R^3$ and $R^4$ is an alkyl, alkenyl or alkaryl group having 6 to 36 carbon atoms. Unsubstituted alkyl, alkenyl or alkaryl groups are especially preferred.

In some embodiments $R^1$ is an alkyl group having 1 to 4 carbon atoms and each of $R^2$, $R^3$ and $R^4$ is an alkyl, alkenyl or alkaryl group having 6 to 36 carbon atoms. Unsubstituted alkyl, alkenyl or alkaryl groups are especially preferred.

In some embodiments $R^1$ is an alkyl group having 1 to 4 carbon atoms, preferably methyl; and each of $R^2$, $R^3$ and $R^4$ is an alkyl or alkenyl group having 6 to 36 carbon atoms, preferably 6 to 20 carbon atoms. Unsubstituted alkyl and alkenyl groups are especially preferred.

In some embodiments each of $R^1$, $R^2$, $R^3$ and $R^4$ have at least 6 carbon atoms.

In some embodiments each of $R^1$, $R^2$, $R^3$ and $R^4$ is an alkyl, alkenyl or alkaryl group having 6 to 36 carbon atoms. Unsubstituted alkyl, alkenyl or alkaryl groups are especially preferred.

In some embodiments each of $R^1$, $R^2$, $R^3$ and $R^4$ is benzyl or an alkyl or alkenyl group having 6 to 36 carbon atoms, for example 8 to 20 carbon atoms. Unsubstituted alkyl and alkenyl groups are especially preferred.

Suitably each of $R^1$, $R^2$, $R^3$ and $R^4$ is an alkyl group; each of $R^3$ and $R^4$ has at least 6 carbon atoms and $R^1$, $R^2$, $R^3$ and $R^4$ together have from 16 to 40 carbon atoms, preferably from 20 to 36 carbon atoms, for example from 20 to 30 carbon atoms. Unsubstituted alkyl groups are especially preferred.

In some embodiments $R^1$ is a $C_1$ to $C_4$ alkyl group, $R^2$ is a $C_1$ to $C_4$ alkyl group, $R^3$ is a $C_6$ to $C_{20}$ alkyl group and Ra is a $C_6$ to $C_{20}$ alkyl group.

In some embodiments $R^1$ is a $C_1$ to $C_4$ alkyl group, $R^2$ is a $C_6$ to $C_{20}$ alkyl group, $R^3$ is a $C_6$ to $C_{20}$ alkyl group and $R^4$ is a $C_6$ to $C_{20}$ alkyl group.

In some embodiments each of $R^1$, $R^2$, $R^3$ and $R^4$ is a $C_6$ to $C_{20}$ alkyl group.

In some embodiments $R^1$ is methyl, $R^2$ is methyl, $R^3$ is a $C_6$ to $C_{20}$ alkyl group and $R^4$ is a $C_6$ to $C_{20}$ alkyl group.

In some embodiments $R^1$ is methyl and each of $R^2$, $R^3$ and $R^4$ is a $C_6$ to $C_{20}$ alkyl group.

In some preferred embodiments $R^1$ is methyl, $R^2$ is methyl, $R^3$ is benzyl and $R^4$ is a $C_8$ to $C_{18}$ alkyl group.

In some preferred embodiments $R^1$ is methyl, $R^2$ is methyl, $R^3$ is methyl and $R^4$ is a $C_{12}$ to $C_{36}$ alkyl group, preferably $C_{20}$ to $C_{30}$ alkyl group In some preferred embodiments $R^1$ is methyl, $R^2$ is methyl, $R^3$ is a $C_8$ to $C_{18}$ alkyl group and $R^4$ is a $C_8$ to $C_{18}$ alkyl group.

In some especially preferred embodiments $R^1$ is methyl, $R^2$ is methyl, $R^3$ is a $C_{10}$ to $C_{14}$ alkyl group and $R^4$ is a $C_{10}$ to $C_{14}$ alkyl group.

In some embodiments $R^1$ is a $C_1$ to $C_4$ alkyl group, $R^2$ is a $C_1$ to $C_4$ alkyl group and each of $R^3$ and $R^4$ comprises a mixture of alkyl groups having 8 to 18 carbon atoms. Suitably such mixtures may be derived from coconut oil.

In some especially preferred embodiments $R^1$ is methyl, $R^2$ is methyl and each of $R^3$ and $R^4$ comprises a mixture of alkyl groups having 8 to 18 carbon atoms. Suitably such mixtures may be derived from coconut oil.

In some embodiments, $R^1$ is methyl, $R^2$ is methyl, $R^3$ is a $C_{12}$ alkyl group and $R^4$ is a $C_{12}$ alkyl group.

In some embodiments $R^1$ is a $C_1$ to $C_4$ alkyl group, $R^2$ is a $C_1$ to $C_4$ alkyl group and each of $R^3$ and $R^4$ comprises a mixture of alkyl or alkenyl groups having 14 to 18 carbon atoms. Suitably such mixtures may be derived from tallow oil or hydrogenated tallow oil.

In some especially preferred embodiments $R^1$ is methyl, $R^2$ is methyl and each of $R^3$ and $R^4$ comprises a mixture of alkyl or alkenyl groups having 14 to 18 carbon atoms. Suitably such mixtures may be derived from tallow oil or hydrogenated tallow oil.

In preferred embodiments $R^1$, $R^2$, $R^3$ and $R^4$ together comprise in total from 16 to 40 carbon atoms, preferably from 20 to 36 carbon atoms, for example from 20 to 30 carbon atoms.

Ar represents a polycyclic aromatic moiety. By polycyclic aromatic moiety we mean to refer to a moiety including at least two aromatic rings, suitably two or more fused aromatic rings. In some embodiments some non-aromatic carbon atoms may be present as part of a polycyclic core. However the polycyclic aromatic moiety Ar is substantially aromatic in character.

The polycyclic aromatic moiety Ar may include one or more substituents. For the avoidance of doubt, any substituents present on the moieties Ar are in addition to the sulfonate residues $SO_3^-$ already indicated as present in the structure of formula (I). Suitably substituents include hydroxyl, alkoxy (especially C1 to C12 alkoxy), amino (NH2), alkyl amino (especially C1 to C12 alkyl amino), dialkyl amino (especially C1 to C12 dialkyl amino), nitro, halo (chloro, bromo, iodo, fluoro), carboxyl, ester (especially C1 to C12 alkyl ester), phenolic ester (especially C1 to C12 phenolic ester) and keto (especially C1 to C12 keto).

In some embodiments the polycyclic aromatic moiety Ar may include one or more heteroatoms as part of the ring, for example as part of an aromatic heterocycle. When the groups Ar comprise heteroatoms these are suitably selected from N, S, O and P.

Preferably the aromatic atoms of the polycyclic aromatic moiety Ar are all carbon atoms.

Preferably the polycyclic aromatic moiety Ar is based on naphthalene, acenapthene, acenaphthylene, fluorene, phenanthrene, anthracene, fluoranthrene, pyrene, benzo[a]anthracene, chrysene, benzo[b]fluoranthrene, benzo[k]fluoranthrene, benzo[a]pyrene, dibenzo[a,h]anthracene, benzo[g,h,i]perylene or indeno[1,2,3,cd]pyrene.

Preferably the polycyclic aromatic moiety Ar is based on a fluorene, naphthalene, anthracene or pyrene moiety, or an isomer thereof.

The compound of formula (I) comprises one or more cations of formula:

and an anionic species of formula which may comprise one or more anionic moieties $SO_3^-$.

The anion suitably comprises a polycyclic aromatic moiety Ar substituted with one or more sulfonate residues $SO_3^-$.

Preferably each aromatic ring in the polycyclic aromatic moiety Ar has 5 to 7 atoms. More preferably each aromatic ring in the polycyclic aromatic moiety Ar has 6 atoms, preferably 6 carbon atoms. However the skilled person will appreciate that since the rings are fused, the total number of atoms in the polycyclic aromatic moiety Ar will be lower than the sum of the number in each ring.

The polycyclic aromatic moiety Ar has at least 2 fused aromatic rings. The polycyclic aromatic moiety Ar may comprise from 2 to 8 fused aromatic rings, suitably from 2 to 5 fused aromatic rings, preferably 2 or 4 fused aromatic rings.

In preferred embodiments the only substituents of the polycyclic aromatic moiety Ar are the sulfonate groups $SO_3^-$ shown in the compound of formula (I).

The polycyclic aromatic moiety Ar contains multiple aromatic rings. Each ring may be substituted with 0, 1 or more than one sulfonate residue $SO_3^-$.

Suitably the anionic portion of the compound of formula (I) is a sulfonated compound based on a fluorene, naphthalene, anthracene or pyrene moiety, or an isomer thereof.

Suitably the anionic portion of the compound of formula (I) is a sulfonated compound based on a naphthalene, anthracene or pyrene moiety, or an isomer thereof.

Preferably the anionic portion of the compound of formula (I) is a sulfonated compound based on a naphthalene, anthracene or pyrene moiety.

In some especially preferred embodiments the anionic portion of the compound of formula (I) is a sulfonated pyrene.

n is at least 1. Preferably n is more than one. Suitably n is 2, 3 or 4. Preferably n=p.

p is at least 1. Preferably p is more than one. Suitably p is from 2 to 6, preferably from 2 to 5. Preferably p is 2, 3 or 4. In some preferred embodiments p is equal to the number of fused aromatic rings in the polycyclic aromatic moiety Ar.

In one preferred embodiment the anionic portion of the compound of formula (I) is a tetrasulfonated pyrene moiety.

Preferably in the compound of formula (I), $R^1$ is hydrogen, benzyl or an alkyl or alkenyl group having 1 to 12 carbon atoms and each of $R^2$, $R^3$ and $R^4$ is benzyl or an alkyl or alkenyl group having 1 to 36 carbon atoms, provided that that at least one of $R^2$, $R^3$ and $R^4$ has at least 6 carbon atoms; the polycyclic aromatic moiety Ar has 2, 3, 4 or 5 fused rings; p is at least 2 and n=p. Unsubstituted alkyl and alkenyl groups are especially preferred.

Preferably in the compound of formula (I), $R^1$ is hydrogen, benzyl or an alkyl group having 1 to 4 carbon atoms and each of $R^2$, $R^3$ and $R^4$ is benzyl or an alkyl or alkenyl group having 1 to 36 carbon atoms, provided that that at least one of $R^2$, $R^3$ and $R^4$ has at least 6 carbon atoms; the polycyclic aromatic moiety Ar has 2 or 4 fused aromatic rings, each of which has 6 carbon atoms; p is at least 2; and n=p. In some such embodiments at least two of $R^2$, $R^3$ and $R^4$ has at least 6 carbon atoms. In some such embodiments each of $R^2$, $R^3$ and $R^4$ has at least 6 carbon atoms. Unsubstituted alkyl and alkenyl groups are especially preferred.

Preferably in the compound of formula (I), $R^1$ is hydrogen or an alkyl group having 1 to 4 carbon atoms; $R^2$ is an alkyl group having 1 to 4 carbon atoms or an alkyl or alkenyl group having 6 to 36 carbon atoms, preferably 8 to 30 carbon atoms; $R^3$ is benzyl, an alkyl group having 1 to 4 carbon atoms or an alkyl or alkenyl group having 6 to 36 carbon atoms, preferably 8 to 30 carbon atoms; and $R^4$ is an alkyl or alkenyl group having 6 to 36 carbon atoms, preferably 8 to 30 carbon atoms; the polycyclic aromatic moiety Ar has 2 or 4 fused aromatic rings, each of which has 6 carbon atoms; p is at least 2; and n=p. Unsubstituted alkyl and alkenyl groups are especially preferred.

Preferably in the compound of formula (I), $R^1$ is hydrogen or an alkyl group having 1 to 4 carbon atoms, $R^2$ is benzyl or an alkyl group having 1 to 4 carbon atoms and each of $R^3$ and $R^4$ is benzyl or an alkyl or alkenyl group having 1 to 36 carbon atoms, provided that that at least one of $R^2$, $R^3$ and $R^4$ has at least 6 carbon atoms; the polycyclic aromatic moiety Ar has 2 or 4 fused aromatic rings, each of which has 6 carbon atoms; p is at least 2; and n=p. Unsubstituted alkyl and alkenyl groups are especially preferred.

Preferably in the compound of formula (I), $R^1$ is an alkyl group having 1 to 4 carbon atoms, $R^2$ is an alkyl group having 1 to 4 carbon atoms, $R^3$ is benzyl or an alkyl or alkenyl group having 1 to 36 carbon atoms and $R^4$ is an alkyl or alkenyl group having 6 to 36 carbon atoms; the polycyclic aromatic moiety Ar has 2 or 4 fused aromatic rings, each of which has 6 carbon atoms; p is at least 2 and n=p. Unsubstituted alkyl and alkenyl groups are especially preferred.

Preferably in the compound of formula (I), $R^1$ is an alkyl group having 1 to 4 carbon atoms, $R^2$ is an alkyl group having 1 to 4 carbon atoms, $R^3$ is benzyl, an alkyl group having 1 to 4 carbon atoms or an alkyl or alkenyl group having 6 to 36 carbon atoms and $R^4$ is an alkyl or alkenyl group having 6 to 36 carbon atoms; the polycyclic aromatic moiety Ar has 2 or 4 fused aromatic rings, each of which has 6 carbon atoms; p is at least 2 and n=p. Unsubstituted alkyl and alkenyl groups are especially preferred.

Preferably in the compound of formula (I), $R^1$ is an unsubstituted alkyl group having 1 to 4 carbon atoms; $R^2$ is an unsubstituted alkyl group having 1 to 4 carbon atoms; $R^3$ is benzyl or an unsubstituted alkyl group having 1 to 4 carbon atoms and $R^4$ is an unsubstituted alkyl or alkenyl group having 10 to 36 carbon atoms or each of $R^3$ and $R^4$ is an unsubstituted alkyl or alkenyl group having 6 to 36 carbon atoms; the polycyclic aromatic moiety Ar has 2 or 4 fused aromatic rings, each of which has 6 carbon atoms; p is at least 2 and n=p.

Preferably in the compound of formula (I), $R^1$ is hydrogen or methyl; $R^2$ is methyl or an unsubstituted alkyl group having 6 to 20 carbon atoms; $R^3$ is methyl, benzyl or an or an unsubstituted alkyl or alkenyl group having 8 to 30 carbon atoms and $R^4$ is an unsubstituted alkyl or alkenyl group having 8 to 30 carbon atoms; the polycyclic aromatic moiety Ar has 2 or 4 fused aromatic rings, each of which has 6 carbon atoms; p is at least 2 and n=p.

Preferably in the compound of formula (I), $R^1$ is hydrogen or methyl; $R^2$ is methyl or an unsubstituted alkyl group having 6 to 20 carbon atoms; $R^3$ is methyl, benzyl or an or an unsubstituted alkyl or alkenyl group having 8 to 30 carbon atoms and $R^4$ is an unsubstituted alkyl or alkenyl group having 8 to 30 carbon atoms; Ar is a pyrene moiety; p is 4 and n is 4.

In an especially preferred embodiments the compound of formula (I) has the structure (II):

or an isomer thereof.

Most preferably the compound of formula (I) has the structure (II).

In one embodiment in structure (II), $R^1=R^2=$methyl, $R^3$ is benzyl and $R^4$ is a $C_{10}$ to $C_{18}$ alkyl group.

Preferably in structure (II), $R^1=R^2=$methyl and each of $R^3$ and $R^4$ is a $C_8$ to $C_{18}$ alkyl group or a mixture of $C_8$ to $C_{18}$ alkyl groups.

In one embodiment in structure (II), $R^1=R^2=$methyl and each of $R^3$ and $R^4$ is a $C_8$ to $C_{18}$ alkyl group or a mixture of $C_{14}$ to $C_{18}$ alkyl or alkenyl groups.

Most preferably in structure (II) $R^1=R^2=$methyl and each of $R^3$ and $R^4$ is a $C_{12}$ alkyl group or a mixture of $C_8$ to $C_{18}$ alkyl groups.

According to a second aspect the present invention there is provided a method of preparing a compound of formula (I):

the method comprising admixing (a) a quaternary ammonium salt, a tertiary amine or a tertiary amine salt with (b) a sulfonated polycyclic aromatic compound.

In some embodiments, $R^1$ is hydrogen and the method of the second aspect involves admixing a tertiary amine of formula $R^2R^3R^4N$ with an acidic sulfonated aromatic compound. By an acidic aromatic compound we mean to refer to an aromatic compound including at least one group $SO_3H$.

In preferred embodiments in which component (a) comprises a quaternary ammonium salt or a tertiary amine salt, the method of the second aspect comprises admixing a compound of formula (III):

(III)

and compound of formula (IV):

wherein Ar is a polycyclic aromatic moiety, p is at least 1, $X^+$ is a proton, an ammonium ion or a metal ion, $R^1$ is hydrogen or an optionally substituted hydrocarbyl group, each of $R^2$, $R^3$ and $R^4$ is independently an optionally substituted hydrocarbyl group, provided that at least one of $R^2$, $R^3$ and $R^4$ has at least 6 carbon atoms and $Y^-$ is an anion.

Preferred features of the second aspect, especially the definitions of $R^1$, $R^2$, $R^3$ and $R^4$, n, p and Ar are as defined in relation to the first aspect.

$X^+$ is a proton, an ammonium ion or a metal ion.

For the avoidance of doubt when $X^+$ is an ammonium ion, it is an unsubstituted ammonium ion $NH_4^+$.

Preferably $X^+$ is a proton or an alkali metal ion. More preferably $X^+$ is a proton or a sodium ion. Most preferably $X^+$ is a sodium ion.

Preferably $Y^-$ is a monovalent anion.

Suitable monovalent anions will be known to the person skilled in the art and include halide, nitrite, methylsulfate, acetate, hydrogen sulfate, hydrogen carbonate, hydroxyl, oxalate, salicylate, carboxylates, nitrates, nitrides, nitrites, hyponitrites, phenates, carbamates, carbonates, and mixtures thereof.

Preferably $Y^-$ is a halide or nitrite ion.

Preferably $Y^-$ is chloride, bromide, iodide or nitrite.

In some preferred embodiments $^-$ is $NO_2^-$.

The method of the second aspect preferably involves admixing a compound of formula (III) and a compound of formula (IV). Suitably the compounds are admixed in the presence of a solvent, suitably with agitation.

Preferred solvents are polar solvents. Suitable solvents include water and water miscible solvents, for example water miscible alcohols. Preferably the compound of formula (III) and the compound of formula (IV) are admixed in a mixture of water and one or more water miscible alcohols, for example ethanol and/or isopropanol.

Suitably the reaction is carried out under ambient conditions.

In some embodiments the compound of formula (I) may precipitate from the reaction mixture and be collected by filtration.

In some embodiments a water immiscible organic solvent in which the compound of formula (I) is soluble may be added to the reaction mixture. Suitable water immiscible organic solvents will be known to the person skilled in the art and include aromatic solvents, for example xylene; aliphatic solvents, for example heptane and isooctane; cycloaliphatic solvents, for example methyl cyclohexane; ketones, for example methyl isobutyl ketone (MIBK); esters, for example ethyl acetate or butyl acetate; cyclic or acylic ethers, for example dibutyl ether, cyclopentyl methyl ether (CPME) and 2-methyl tetrahydrofuran; higher alcohols, for example n-butanol, 2-butanol, amyl alcohol and n-octanol; polyhydric alcohols and ethers thereof, for example ethylene glycol and ethylene glycol dimethyl ether; and halogenated solvents, for example dichloromethane, chloroform, carbon tetrachloride or 1,2-dichloroethane. In such embodiments the method suitably involves extracting the compound of formula (I) into said water immiscible organic solvent. The method may include an additional washing step.

When the compound of formula (I) is obtained in an organic solvent, for example an aromatic solvent, it may be directly used in such a solvent.

The compound of the first aspect of the present invention suitably has fluorescent properties. By this we mean that the compound is able to absorb electromagnetic radiation at a first wavelength and emit electromagnetic radiation at a second different wavelength.

Suitably the first wavelength is from 340 to 410 nm and the second wavelength is from 400 to 500 nm.

The compound of the first aspect of the present invention may suitably find utility as a fluorescent marker. In particular the compound may be useful as a marker in a fuel additive composition.

According to a third aspect of the present invention there is provided a composition comprising a compound of formula (I):

(I)

wherein p is at least 1, n is at least one and less than or equal to p, Ar is a polycyclic aromatic moiety, $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms.

Preferred features of the third aspect, especially the definitions of $R^1$, $R^2$, $R^3$ and $R^4$, n, p and Ar are as defined in relation to the first aspect.

Suitably the composition of the third aspect comprises a compound of formula (I) and one or more further components.

In some embodiments the composition of the third aspect comprises the compound of formula (I) and one or more solvents.

Preferred solvents are organic solvents.

Suitable solvents include aliphatic and aromatic solvents, polar and non-polar solvents.

Preferred solvents include aromatic solvents and alcohols.

In some preferred embodiments the composition of the third aspect is an additive composition for fuels, the additive composition comprising:
a compound of formula (I);
one or more fuel additives; and optionally
one or more solvents.

For the avoidance of doubt the one or more additives are present in addition to the compound of formula (I).

Preferred solvents are as defined above. Suitable solvents will depend on the nature of the other components present in the composition and the nature of fuel in which the additive composition will be used.

Suitably the additive composition includes one or more additives for improving the properties of a fuel and/or preventing damage to engines or other surfaces that come into contact with the fuel and/or reducing the environmental impact of combusting a fuel.

Suitably the additive composition comprises a compound of formula (I) and one or more additives selected from: detergents, dispersants, antioxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, static dissipator additives, combustion improvers, wax anti-settling agents, cold flow improvers, cetane improvers, dyes, other markers and drag reducers.

Preferred additives falling within these classes will be known to the person skilled in the art.

The nature of the additive will depend on the nature of the fuel in which it is intended to be used.

Preferably the compound of formula (I) is present in the additive composition in an amount of from 0.01 to 20 wt %, more preferably from 0.05 to 10 wt %, suitably from 0.1 to 5 wt %, for example from 0.1 to 2 wt %.

Suitable additives for use in fuel compositions are further defined herein.

The concentration of the or each additive present in the additive composition will depend on the intended dilution ratio in the fuel and the necessary level needed to achieve the desired performance whilst minimising any negative effects.

Preferably the additive composition comprises a corrosion inhibitor and a compound of formula (I). It may comprise a corrosion inhibitor a compound of formula (I) and one or more further additives.

In one embodiment the corrosion inhibitor is included in the additive composition in an amount of from 1 to 99 wt %, suitably 10 to 95 wt %, preferably 30 to 90 wt %, more preferably 60 to 80 wt %, suitably from 65 to 75 wt %.

According to a fourth aspect of the present invention there is provided a fuel composition comprising a fuel, one or more additives and a compound of formula (I).

For the avoidance of doubt the one or more additives are present in addition to the compound of formula (I).

Preferred features of the compound of formula (I) are as defined in relation to the first aspect.

The compound of formula (I) is suitably present in the fuel compositions of the present invention in an amount of from 0.01 to 2000 ppb.

For the avoidance of doubt, in this specification any reference to ppb is to parts per billion by weight and references to ppm is to parts per million by weight.

In some preferred embodiments the fuel composition comprises a corrosion inhibitor and a compound of formula (I).

The compounds of formula (I) are suitably soluble in fuels, especially hydrocarbon fuels, for example diesel or gasoline. Preferably they are not water soluble.

According to a fifth aspect of the present invention there is provided a method of preparing a fuel composition, the method comprising:
  preparing an additive composition of the third aspect; and
  dosing said additive composition into a fuel.

In some embodiments the fuel comprises ethanol. In one embodiment the fuel may consist essentially of ethanol.

In some embodiments the fuel comprises gasoline. In one embodiment the fuel may consist essentially of gasoline.

Thus the invention suitably provides a gasoline composition comprising gasoline, one or more additives and a compound of formula (I).

By the term "gasoline", it is meant a liquid fuel for use with spark ignition engines (typically or preferably containing primarily or only C4-C12 hydrocarbons) and satisfying international gasoline specifications, such as ASTM D-439 and EN228. The term includes blends of distillate hydrocarbon fuels with oxygenated components such as alcohols or ethers for example methanol, ethanol, butanol, methyl t-butyl ether (MTBE), ethyl t-butyl ether (ETBE), as well as the distillate fuels themselves.

The present invention finds particular utility in blends of mineral gasoline and ethanol. Preferably the fuel composition of the present invention comprises from 1 to 99% vol ethanol and from 99 to 1% vol gasoline, preferably from 2 to 80% vol ethanol and from 98 to 20% vol gasoline, suitably from 3 to 70% vol ethanol and from 97 to 30% vol gasoline, preferably from 5 to 40% vol ethanol and from 95 to 60% vol gasoline, more preferably from 8 to 20% vol ethanol and from 92 to 80% vol gasoline. In especially preferred embodiments the fuel composition of the present invention comprises from 10 to 15% vol ethanol and from 90 to 85% vol gasoline.

Fuels comprising 100% vol ethanol or 100% vol gasoline are also within the scope of the invention.

In this specification references to the gasoline fuel composition are intended to include compositions comprising blends of gasoline and ethanol.

The gasoline fuel compositions of the present invention contain one or more additives. These additives may be selected from any that are conventionally added to gasoline. Preferably the one or more additives are selected from detergents, dispersants, anti-oxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, static dissipator additives and combustion improvers.

In one preferred embodiment the gasoline fuel composition comprises a corrosion inhibitor.

In a preferred embodiment the method of the fifth aspect of the present invention involves:
  preparing an additive composition of the third aspect;
  dosing said additive composition into an ethanol component of a fuel composition; and
  blending said ethanol component with a gasoline fuel.

Suitably the additive composition of the third aspect is included in the ethanol component in an amount of from 0.01 to 1000 ppm, preferably from 0.1 to 500 ppm, suitably from 0.5 to 200 ppm, preferably from 0.8 to 95 ppm, for example from 10 to 70 ppm or 20 to 35 ppm.

The ethanol component preferably comprises from 0.001 to 10 ppm of a compound of formula (I), preferably from 0.002 to 1 ppm, suitably from 0.004 to 0.5 ppm, preferably from 0.05 to 0.4 ppm, for example from 0.1 to 0.2 ppm.

The ethanol component preferably comprises from 0.01 to 500 ppm of a corrosion inhibitor, preferably from 0.1 to 200 ppm, suitably from 0.5 to 70 ppm, preferably from 5 to 50 ppm, for example from 15 to 25 ppm.

The ethanol component is preferably blended with the gasoline fuel in an amount of from 5 to 20 vol %, more preferably 10 to 15 vol %.

The gasoline fuel composition preferably comprises from 0.01 to 500 ppb of a compound of formula (I), preferably from 0.1 to 200 ppb, suitably from 0.3 to 75 ppb, preferably from 5 to 60 ppb, for example from 10 to 30 ppb.

The gasoline fuel composition preferably comprises from 0.01 to 100 ppm of a corrosion inhibitor, preferably from 0.1 to 200 ppm, suitably from 0.1 to 10 ppm, preferably from 0.5 to 8 ppm, for example from 1 to 4 ppm.

In some embodiments the fuel composition of the fifth aspect is a diesel fuel composition.

By diesel fuel we include any fuel suitable for use in a diesel engine, either for road use or non-road use. This includes, but is not limited to, fuels described as diesel, marine diesel, heavy fuel oil, industrial fuel oil etc.

The diesel fuel composition of the present invention may comprise a petroleum-based fuel oil, especially a middle distillate fuel oil. Such distillate fuel oils generally boil within the range of from 110° C. to 500° C., e.g. 150° C. to 400° C. The diesel fuel may comprise atmospheric distillate or vacuum distillate, cracked gas oil, or a blend in any proportion of straight run and refinery streams such as thermally and/or catalytically cracked and hydro-cracked distillates.

The diesel fuel composition of the present invention may comprise non-renewable Fischer-Tropsch fuels such as those described as GTL (gas-to-liquid) fuels, CTL (coal-to-liquid) fuels and OTL (oil sands-to-liquid).

The diesel fuel composition of the present invention may comprise a renewable fuel such as a biofuel composition or biodiesel composition.

The diesel fuel composition may comprise 1st generation biodiesel. First generation biodiesel contains esters of, for example, vegetable oils, animal fats and used cooking fats. This form of biodiesel may be obtained by transesterification of oils, for example rapeseed oil, soybean oil, safflower oil, palm oil, corn oil, peanut oil, cotton seed oil, tallow, coconut oil, physic nut oil (Jatropha), sunflower seed oil, used cooking oils, hydrogenated vegetable oils or any mixture thereof, with an alcohol, usually a monoalcohol, in the presence of a catalyst.

The diesel fuel composition may comprise second generation biodiesel. Second generation biodiesel is derived from renewable resources such as vegetable oils and animal fats and processed, often in the refinery, often using hydro-processing such as the H-Bio process developed by Petrobras. Second generation biodiesel may be similar in properties and quality to petroleum based fuel oil streams, for example renewable diesel produced from vegetable oils, animal fats etc. and marketed by ConocoPhillips as Renewable Diesel and by Neste as NExBTL.

The diesel fuel composition of the present invention may comprise third generation biodiesel. Third generation biodiesel utilises gasification and Fischer-Tropsch technology including those described as BTL (biomass-to-liquid) fuels. Third generation biodiesel does not differ widely from some second generation biodiesel, but aims to exploit the whole plant (biomass) and thereby widens the feedstock base.

The diesel fuel composition may contain blends of any or all of the above diesel fuel compositions.

In some embodiments the diesel fuel composition of the present invention may be a blended diesel fuel comprising bio-diesel. In such blends the bio-diesel may be present in an amount of, for example up to 0.5%, up to 1%, up to 2%, up to 3%, up to 4%, up to 5%, up to 10%, up to 20%, up to 30%, up to 40%, up to 50%, up to 60%, up to 70%, up to 80%, up to 90%, up to 95% or up to 99%.

In some embodiments the diesel fuel composition may comprise 100% biodiesel.

The diesel fuel composition of the present invention may include one or more additives. These may be selected from any additives which are commonly found in diesel fuels. Preferably the one or more additives are selected from antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, odour masks, drag reducers and static dissipator additives. Examples of suitable amounts of each of these types of additives will be known to the person skilled in the art.

In one preferred embodiment the diesel fuel composition comprises a corrosion inhibitor. This is preferably present in an amount of from 0.1 to 200 ppm, preferably 0.5 to 50 ppm, more preferably 2 to 10 ppm.

The compound of formula (I) is suitably present in the diesel fuel compositions of the present invention in an amount of from 0.01 to 1000 ppb, for example 0.1 to 200 ppb.

Preferably the fuel composition of the fourth aspect comprises:

a fuel selected from gasoline, diesel and blends of gasoline or diesel with biofuels (for example gasoline, ethanol or mixtures thereof or diesel, biodiesel or mixtures thereof);

a first additive selected from anti-icing agents, friction modifiers, octane improvers, anti-valve-seat recession additives, antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, odour masks, drag reducers and static dissipator additives;

a compound of formula (I); and optionally one or more further additives.

Preferably the first additive is a corrosion inhibitor.

Preferred corrosion inhibitors for use herein include low molecular weight (<1000) amines (including mono-, di-, tri- and polyamines), carboxylic acids (including mono-, di-, tri- and polycarboxylic acids) and their functional derivatives (for example esters), etheramines, imines, amides, imides, N-oxides, imidazolines and thiadiazoles. Combinations of the above materials may be used.

Carboxylic acids or derivatives thereof may be especially preferred as corrosion inhibitors, including succinic acid or succinic anhydride derivatives, for example tetrapropenyl succinic acid, tetrapropenyl succinic anhydride or dodecenyl succinic acid.

Dimer acids represent a further class of preferred corrosion inhibitors. Dimer acids include products resulting from the dimerization of unsaturated fatty acids and generally contain an average from about 18 to about 44, or from about 28 to about 40 carbon atoms. Trimer acids may also be present. Dimer acids are described in U.S. Pat. Nos. 2,482,760, 2,482,761, 2,731,481, 2,793,219, 2,964,545, 2,978,468, 3,157,681, and 3,256,304.

Carboxylic acid based corrosion inhibitors may optionally be used in combination with substituted amines, to provide 'buffered' corrosion inhibitors. Examples of amines used in this manner include dicyclohexylamine, N,N-dimethylcyclohexylamine or fatty amines. Fatty amines may be defined as those containing from about 8 to about 30, or from about 12 to about 24 carbon atoms.

Examples of commercially available corrosion inhibitors include the products DCI-4A, DCI-6A, DCI-11 and DCI-30, available from Innospec and corrosion inhibitors available from other fuel additive producers, for example Nalco, GE, Afton, Dorf Ketal and Lubrizol.

The concentration of one or more further additives present in the fuel composition in the present invention will depend on the nature of the fuel and the nature of the additive.

Preferably the fuel composition of the fifth aspect comprises:
 a fuel selected from gasoline, diesel and blends of gasoline or diesel with biofuels (for example, blends of gasoline and ethanol or blends of diesel and biodiesel);
 corrosion inhibitor;
 a compound of formula (I); and
 optionally one or more further additives.

The present invention relates to fuel compositions comprising an additive and a compound of formula (I).

Suitably the compound of formula (I) has fluorescent properties.

According to an sixth aspect of the present invention there is provided the use of a compound of formula (I) as a fluorescent marker.

The compound of formula (I) is preferably as defined in relation to the first aspect.

According to a seventh aspect of the present invention there is provided a method of determining the presence of an additive in a fuel composition comprising said additive and a compound of formula (I), the method comprising applying electromagnetic radiation having a first wavelength to said fuel composition; and determining the emission of electromagnetic radiation from the compound of formula (I) at a second wavelength.

The second wavelength is suitably different to the first wavelength.

The compound of formula (I) is preferably as defined in relation to the first aspect.

In some embodiments the method of the seventh aspect may be used to determine presence of an additive that was added to the fuel as part of an additive composition comprising the additive, the compound of formula (I) and optionally one or more further additives. Thus the method can be used to determine that an additive composition has been dosed into a fuel.

The method of the second aspect may be used qualitatively in a verification process to ensure that the correct additive composition has been used. In such embodiments determining the emission of electromagnetic radiation at a second wavelength may simply involve observing fluorescence, for example by sight. Alternatively a device, for example a spectrophotometer, could be used to detect emission at the appropriate wavelength. In some embodiments the device may include an indicator (for example one which produces a sound or a visual effect) to demonstrate when electromagnetic radiation at a second wavelength is emitted.

Applying electromagnetic radiation at the first wavelength may be achieved by any suitable means. Such means will be known to the person skilled in the art.

In some embodiments the present invention may involve quantitatively measuring the amount of light emitted from the fuel composition and thereby determining the concentration of an additive or additive composition present in the fuel composition. In such embodiments a marker is included in an additive composition in an amount proportional to a particular additive. Suitably when an additive or additive composition is dosed into a fuel oil a fixed relative proportion of the fluorescent marker is also dosed into the fuel. Thus measurement of emission from the fluorescent marker allows a calculation to be performed to determine the concentration of the additive or additive composition in the fuel composition.

In some embodiments the method of the seventh aspect may be used to determine the concentration of one particular additive present in a fuel composition. In some embodiments the method may be used to determine the concentration of an additive composition that has been dosed into a fuel composition. Such an additive composition may comprise a number of different additives and a compound of formula (I).

According to an eighth aspect of the present invention there is provided a method of determining the concentration of a first additive in a fuel composition comprising said first additive and a compound of formula (I), the compound of formula (I) being present in the fuel composition at a concentration that is proportional to the concentration of the first additive; the method comprising: applying electromagnetic radiation having a first wavelength to said fuel composition; measuring emission of electromagnetic radiation from the compound of formula (I) at a second wavelength; and calculating from the level of emission at said second wavelength the concentration of the first additive in the fuel composition.

The compound of formula (I) is preferably as defined in relation to the first aspect.

The present invention may suitably provide a method of determining the concentration of an additive composition that has been dosed into a fuel composition, wherein the additive composition comprises a compound of formula (I) and at least one further additive; the method comprising: applying electromagnetic radiation having a first wavelength to said fuel composition; measuring emission of electromagnetic radiation from the compound of formula (I) at a second wavelength; and calculating from the level of emission at said second wavelength the concentration of the compound of formula (I) in the fuel composition.

Calculation of the concentration of the compound of formula (I) in the fuel composition allows the concentration of the additive composition that was dosed into the fuel to be determined.

Application of radiation at a first wavelength and measurement of emission at a second wavelength may be carried out by any suitable means. The provision of a suitable device will be within the competence of a person skilled in the art. In some embodiments the device may be programmed to perform a calculation based on the level of radiation emitted at the second wavelength and thereby provide directly the concentration of the additive present in the fuel.

According to an ninth aspect of the present invention there is provided a kit for determining the concentration of a compound of formula (I) in a fuel composition, the kit comprising means for applying electromagnetic radiation having a first wavelength to said fuel composition; and means for measuring emission of electromagnetic radiation at a second wavelength.

Preferably the kit comprises means for quantitatively measuring the level of emission of electromagnetic radiation at a second wavelength.

Suitably the means for applying electromagnetic radiation having a first wavelength to said fuel composition and means for measuring emission of electromagnetic radiation at a second wavelength are provided by the same device, suitably a handheld device.

Suitably the kit comprises a fluorimeter.

In some embodiments the kit comprises means for calculating the relative concentration of an additive or additive composition based on the measured concentration of the compound of formula (I). Such means may be a chart or graph, or an electronic calculator. Such an electronic calculator may be incorporated into the device.

The compounds of formula (I) are particularly useful as fluorescent markers as they are not as strongly coloured in the concentrations of which they are used and thus do not affect the colour of a fuel or additive composition into which they are dosed. They also have good solubility in the additive and fuel compositions in which they are used.

Suitably compounds of formula (I) of the present invention do not strongly absorb visible light. Preferred compounds of the present invention have no absorption peaks in the UV—visible spectrum with an molar extinction coefficient greater than 5000 M−1 cm−1, in the wavelength range 400 nm to 750 nm, when run as a 0.025 mg/mL solution in methanol.

Preferably in the compound of formula (I), $R^1$ is hydrogen or an alkyl group having 1 to 4 carbon atoms, $R^2$ is benzyl or an alkyl group having 1 to 4 carbon atoms and each of $R^3$ and $R^4$ is benzyl or an alkyl or alkenyl group having 1 to 36 carbon atoms, provided that that at least one of $R^2$, $R^3$ and $R^4$ has at least 6 carbon atoms; the polycyclic aromatic moiety Ar has 2 or 4 fused aromatic rings, each of which has 6 carbon atoms; p is at least 2; n=p; and the compound has no absorption peaks in the UV—visible spectrum with an molar extinction coefficient greater than 5000 M−1 cm−1, in the wavelength range 400 nm to 750 nm, when run as a 0.025 mg/mL solution in methanol. Unsubstituted alkyl and alkenyl groups are especially preferred.

Preferably in the compound of formula (I), $R^1$ is an alkyl group having 1 to 4 carbon atoms, $R^2$ is an alkyl group having 1 to 4 carbon atoms, $R^3$ is benzyl or an alkyl or alkenyl group having 1 to 36 carbon atoms and $R^4$ is an alkyl or alkenyl group having 6 to 36 carbon atoms; the polycyclic aromatic moiety Ar has 2 or 4 fused aromatic rings, each of which has 6 carbon atoms; p is at least 2; n=p; and the compound has no absorption peaks in the UV—visible spectrum with an molar extinction coefficient greater than 5000 M−1 cm−1, in the wavelength range 400 nm to 750 nm, when run as a 0.025 mg/mL solution in methanol. Unsubstituted alkyl and alkenyl groups are especially preferred.

Preferably in the compound of formula (I), $R^1$ is an alkyl group having 1 to 4 carbon atoms, $R^2$ is an alkyl group having 1 to 4 carbon atoms, $R^3$ is benzyl, an alkyl group having 1 to 4 carbon atoms or an alkyl or alkenyl group having 6 to 36 carbon atoms and $R^4$ is an alkyl or alkenyl group having 6 to 36 carbon atoms; the polycyclic aromatic moiety Ar has 2 or 4 fused aromatic rings, each of which has 6 carbon atoms; p is at least 2; n=p; and the compound has no absorption peaks in the UV—visible spectrum with an molar extinction coefficient greater than 5000 M−1 cm−1, in the wavelength range 400 nm to 750 nm, when run as a 0.025 mg/mL solution in methanol. Unsubstituted alkyl and alkenyl groups are especially preferred.

Preferably in the compound of formula (I), $R^1$ is an unsubstituted alkyl group having 1 to 4 carbon atoms; $R^2$ is an unsubstituted alkyl group having 1 to 4 carbon atoms; $R^3$ is benzyl or an unsubstituted alkyl group having 1 to 4 carbon atoms and $R^4$ is an unsubstituted alkyl or alkenyl group having 10 to 36 carbon atoms or each of $R^3$ and $R^4$ is an unsubstituted alkyl or alkenyl group having 6 to 36 carbon atoms; the polycyclic aromatic moiety Ar has 2 or 4 fused aromatic rings, each of which has 6 carbon atoms; p is at least 2; n=p; and the compound has no absorption peaks in the UV—visible spectrum with an molar extinction coefficient greater than 5000 M−1 cm−1, in the wavelength range 400 nm to 750 nm, when run as a 0.025 mg/mL solution in methanol.

Preferably in the compound of formula (I), $R^1$ is hydrogen or methyl; $R^2$ is methyl or an unsubstituted alkyl group having 6 to 20 carbon atoms; $R^3$ is methyl, benzyl or an or an unsubstituted alkyl or alkenyl group having 8 to 30 carbon atoms and $R^4$ is an unsubstituted alkyl or alkenyl group having 8 to 30 carbon atoms; the polycyclic aromatic moiety Ar has 2 or 4 fused aromatic rings, each of which has 6 carbon atoms; p is at least 2; n=p; and the compound has no absorption peaks in the UV—visible spectrum with an molar extinction coefficient greater than 5000 M−1 cm−1, in the wavelength range 400 nm to 750 nm, when run as a 0.025 mg/mL solution in methanol.

Preferably in the compound of formula (I), $R^1$ is hydrogen or methyl; $R^2$ is methyl or an unsubstituted alkyl group having 6 to 20 carbon atoms; $R^3$ is methyl, benzyl or an or an unsubstituted alkyl or alkenyl group having 8 to 30 carbon atoms and $R^4$ is an unsubstituted alkyl or alkenyl group having 8 to 30 carbon atoms; Ar is a pyrene moiety; n is 4; p is 4: and the compound has no absorption peaks in the UV—visible spectrum with an molar extinction coefficient greater than 5000 M−1 cm−1, in the wavelength range 400 nm to 750 nm, when run as a 0.025 mg/mL solution in methanol.

The present invention will now be further defined with reference to the following non-limiting examples.

General Procedures

UV—visible spectroscopy was carried out using a Lambda 25 Spectrometer (Perkin Elmer, Massachusetts, US) using a quartz glass cuvette with a 1 cm path length.

Fluorescence measurements were taken using a SP-350 handheld fluorimeter (Pyxis Laboratories, Colorado, US).

EXAMPLE 1

Synthesis of 1,3,6,8-Pyrenetetrasulfonic Acid Tetra(Dicocodimethylammonium) Salt Pyrene-1,3,6,8-sulfonic acid tetrasodium salt (305 g, 0.5 mol) was dissolved in water (2 L) in a 5 L glass separating funnel. Dicocodimethylammonium nitrite (75 wt % solution in isopropanol, 1900 g) was added over 5 minutes. The separating funnel was stoppered and vigorously shaken for 5 minutes, with periodic venting, then placed on a retort stand. The solid product, which formed immediately upon mixing, floated to the top of the liquid phase. The aqueous phase was carefully run off, avoiding the loss of solid, then the solid was washed with deionized water (2×1 L), running off the water washes in the same manner. The resulting solid suspension was transferred to a vacuum flask using a 1:1 mixture (by volume) of ethanol and toluene (1 L). The solution was azeotropically dried using a rotary evaporator (85° C.) then concentrated in vacuo to give 1,3,6,8-pyrenetetrasulfonic acid tetra(dicocodimethylammonium) salt as a waxy, peach coloured solid.

Using fluorimetric analysis, the product has an approximate excitation wavelength ($\lambda_{ex}$) of 365 nm and an approximate emission wavelength ($\lambda_{em}$) of 410 nm.

Figure 1:
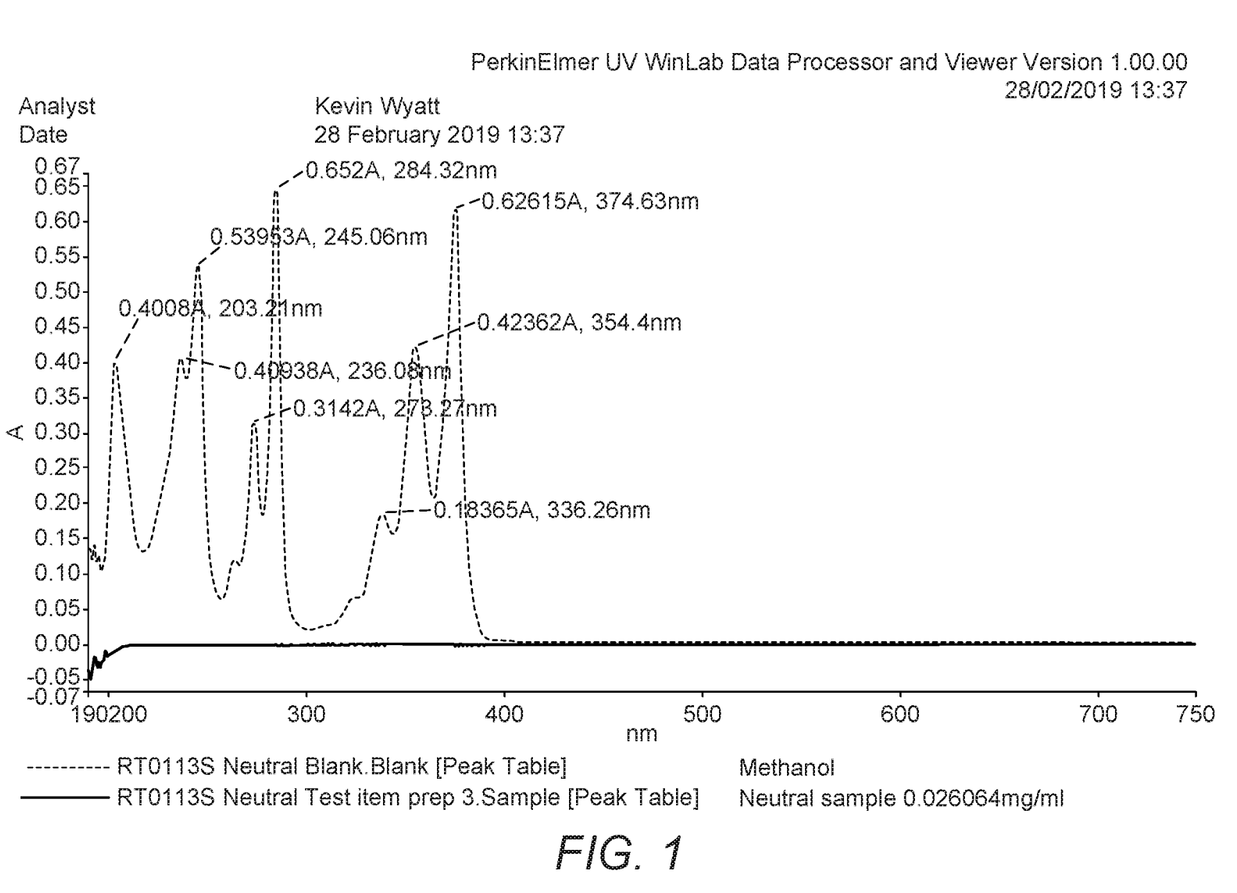
FIG. 1 is a graph showing an absence of significant absorbance peaks in the visible region (380-750 nm) of the present invention.

The UV—visible spectrum was measured (0.026 mg/mL in methanol) and showed an absence of significant absorbance peaks in the visible region (380×750 nm). This is shown in FIG. 1.

EXAMPLE 2

Attempted synthesis of further 1,3,6,8-pyrenetetrasulfonic acid quaternary ammonium salts Using a method analogous to that described in example 1, the reaction of the following quaternary ammonium salts with pyrene-1,3,6,8-sulfonic acid tetrasodium salt was attempted.

| Quaternary ammonium salt | Precipitate Formed? |
| --- | --- |
| ammonium chloride | No |
| tetraethylammonium iodide | No |
| tetrapropylammonium bromide | No |
| tetrabutylammonium iodide | No |
| benzyldimethyl-n-tetradecylammonium chloride | Yes |
| dicocodimethylammonium chloride | Yes |

EXAMPLE 3

Fluorescence Characteristics of a Fuel Additive Package Comprising 1,3,6,8-Pyrenetetrasulfonic Acid Tetra(Dicocodimethylammonium) Salt A fuel additive composition was prepared, comprising a known corrosion inhibiting compound of the prior art and methanol solvent as the major components. The composition additionally comprised the marker compound of Example 1 at a concentration of 0.498 wt % (as active material).

The fuel additive composition was then dosed into ethanol at a range of treat rates (as the additive package) between 0 and 108.48 parts per million by weight (ppm). After mixing, each sample was then analysed in triplicate by fluorimetry ($\lambda_{ex}$ 365 nm, $\lambda_{em}$ 410 nm) using the SP-350 handheld fluorimeter. The fluorimetric response was reported in calibrated units (cu).

Figure 2:
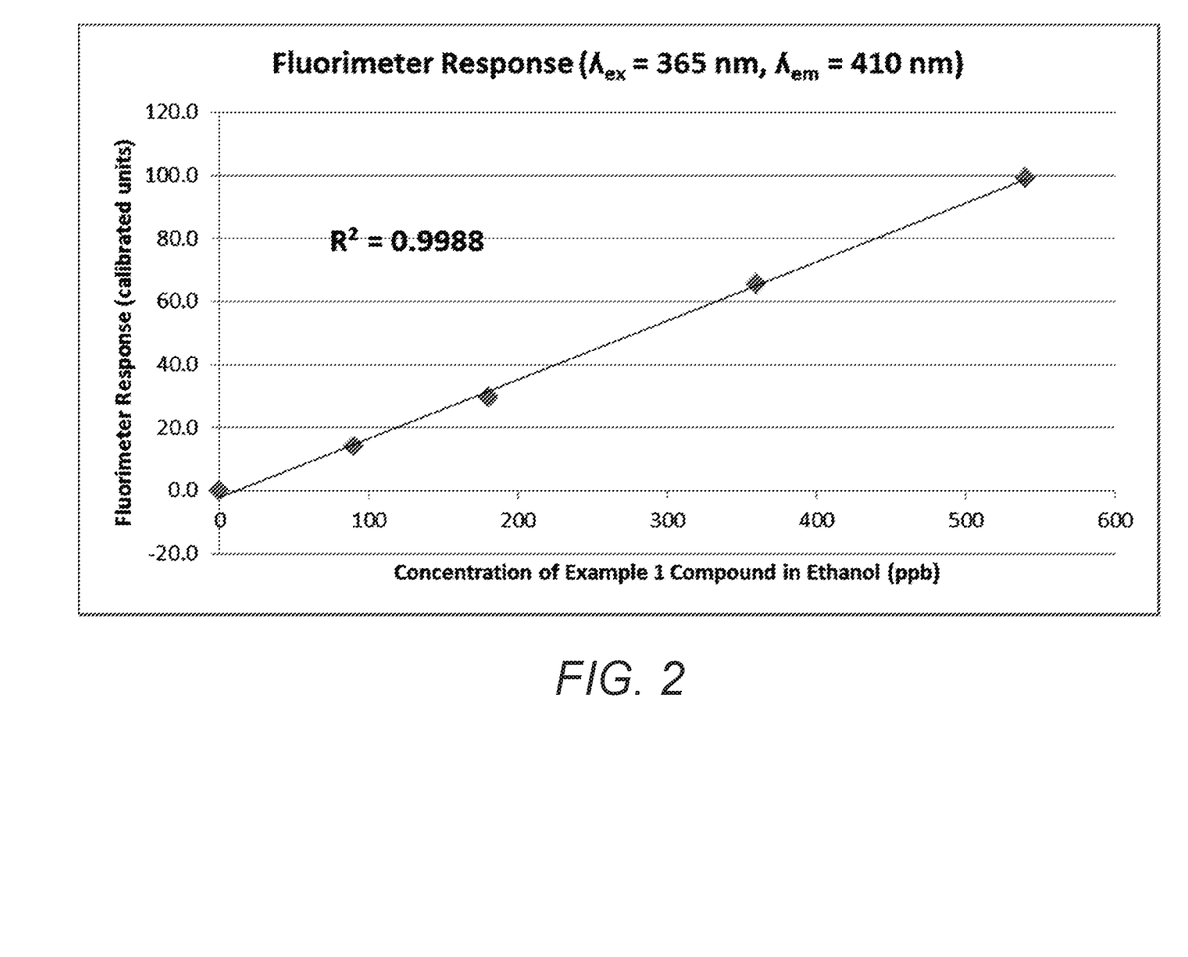
FIG. 2 is a graph plotting Fluorimetric response against marker concentration of the present invention.

Based on the fuel additive composition treat rates and the concentration of the compound of Example 1 (as active) in the additive composition, the final concentration of the invention compound (marker) in the ethanol was calculated (parts per billion by weight, ppb). The results are shown below. Fluorimetric response was plotted against marker concentration; this is shown in FIG. 2.

The plot showed excellent linearity of response ($R^2$=0.9988) in a marker concentration range between 0 and 540 ppb.

| Treat rate of fuel additive composition in Ethanol (ppm) | Concentration of Example 1 compound in Ethanol (ppb) | Fluorimeter Response (calibrated units) |
| --- | --- | --- |
| 0 | 0 | 0.0 |
| 0 | 0 | 0.0 |
| 0 | 0 | 0.0 |
| 18.08 | 90.0384 | 14.0 |
| 18.08 | 90.0384 | 14.2 |
| 18.08 | 90.0384 | 13.9 |
| 36.16 | 180.0768 | 29.6 |
| 36.16 | 180.0768 | 29.4 |
| 36.16 | 180.0768 | 29.9 |
| 72.32 | 360.1536 | 65.4 |
| 72.32 | 360.1536 | 65.4 |
| 72.32 | 360.1536 | 65.6 |
| 108.48 | 540.2304 | 99.1 |
| 108.48 | 540.2304 | 99.3 |
| 108.48 | 540.2304 | 99.0 |

The invention claimed is:

1. A compound of formula (I):

(I)

wherein p is 2 or 4, n is at least 1 and less than or equal to p; Ar is a polycyclic aromatic moiety based on a fluorene, anthracene or pyrene moiety, or an isomer thereof, $R^1$ is hydrogen or an unsubstituted alkyl, alkenyl or aralkyl group and each of $R^2$, $R^3$ and $R^4$ is independently an unsubstituted alkyl, alkenyl or aralkyl group, provided that at least one of $R^2$, $R^3$ and $R^4$ has at least 6 carbon atoms.

2. A method of preparing a compound of formula (I):

(I)

the method comprising admixing (a) a quaternary ammonium salt, a tertiary amine or a tertiary amine salt with (b) a sulfonated polycyclic aromatic compound; wherein p is 2 or 4, n is at least 1 and less than or equal to p; Ar is a polycyclic aromatic moiety based on a fluorene, anthracene or pyrene moiety, or an isomer thereof, $R^1$ is hydrogen or an unsubstituted alkyl, alkenyl or aralkyl group and each of $R^2$, $R^3$ and $R^4$ is independently an unsubstituted alkyl, alkenyl or aralkyl group, provided that at least one of $R^2$, $R^3$ and $R^4$ has at least 6 carbon atoms.

3. The method of preparing a compound of formula (I) according to claim 2, wherein component (a) comprises a quaternary ammonium salt or a tertiary amine salt, and the method involves admixing a compound of formula (III):

(III)

and compound of formula (IV):

(IV)

wherein Ar is a polycyclic aromatic moiety based on a fluorene, anthracene or pyrene moiety, or an isomer thereof, p is 2 or 4, $X^+$ is a proton, an ammonium ion or a metal ion, $R^1$ is hydrogen or an unsubstituted alkyl, alkenyl or aralkyl group, each of $R^2$, $R^3$ and $R^4$ is independently an unsubstituted alkyl, alkenyl or aralkyl group, provided that at least one of $R^2$, $R^3$ and $R^4$ has at least 6 carbon atoms and $Y^-$ is an anion.

4. A composition comprising a compound of formula (I):

(I)

wherein p is 2 or 4, n is at least one and is less than or equal to p; Ar is a polycyclic aromatic moiety based on a fluorene, anthracene or pyrene moiety, or an isomer thereof, $R^1$ is hydrogen or an unsubstituted alkyl, alkenyl or aralkyl group and each of $R^2$, $R^3$ and $R^4$ is independently an unsubstituted alkyl, alkenyl or aralkyl group, provided that at least one of $R^2$, $R^3$ and $R^4$ has at least 6 carbon atoms.

5. The composition according to claim 4, wherein said composition is an additive composition for a fuel and said composition further comprises one or more fuel additives.

6. A fuel composition comprising a fuel, one or more additives and a compound of formula (I):

wherein p is at least 1, n is at least 1 and is less than or equal to p; Ar is a polycyclic aromatic moiety, $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms.

7. The fuel composition according to claim 6 wherein the fuel comprises gasoline, ethanol or mixtures thereof.

8. The fuel composition according to claim 6 wherein the fuel comprises diesel.

9. A method of preparing a fuel composition, the method comprising:
preparing an additive composition comprising a compound of formula (I):

wherein p is at least 1, n is at least 1 and is less than or equal to p; Ar is a polycyclic aromatic moiety, $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms; and
dosing said additive composition into a fuel.

10. The method according to claim 9 wherein said dosing step comprises dosing said additive composition into an ethanol component of a fuel composition; and wherein said method further comprises blending said ethanol component with a gasoline fuel.

11. A method of determining the presence of an additive in a fuel composition comprising said additive and a compound of formula (I):

wherein p is at least 1, n is at least 1 and is less than or equal to p; Ar is a polycyclic aromatic moiety, $R^1$ is hydrogen or an optionally substituted hydrocarbyl group and each of $R^2$, $R^3$, and $R^4$ is independently an optionally substituted hydrocarbyl group, provided that at least one of $R^2$, $R^3$ and $R^4$ has at least 6 carbon atoms, the method comprising applying electromagnetic radiation having a first wavelength to said fuel composition; and determining the emission of electromagnetic radiation from the compound of formula (I) at a second wavelength.

12. A method of determining the concentration of a first additive in a fuel composition comprising said first additive and a compound of formula (I):

wherein p is at least 1, n is at least 1 and is less than or equal to p; Ar is a polycyclic aromatic moiety, $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms, the compound of formula (I) being present in the fuel composition at a concentration that is proportional to the concentration of the first additive; the method comprising: applying electromagnetic radiation having a first wavelength to said fuel composition; measuring emission of electromagnetic radiation from the compound of formula (I) at a second wavelength; and calculating from the level of emission at said second wavelength the concentration of the first additive in the fuel composition.

13. A method of determining the concentration of an additive composition that has been dosed into a fuel composition, wherein the additive composition comprises a compound of formula (I):

wherein p is at least 1, n is at least 1 and is less than or equal to p; Ar is a polycyclic aromatic moiety, $R^1$ is hydrogen or an optionally substituted hydrocarbyl group and each of $R^2$, $R^3$ and $R^4$ is independently an optionally substituted hydrocarbyl group, provided that at least one of $R^2$, $R^3$ and $R^4$ has at least 6 carbon atoms and at least one further additive; the method comprising: applying electromagnetic radiation having a first wavelength to said fuel composition; measuring emission of electromagnetic radiation from the compound of formula (I) at a second wavelength; and calculating from the level of emission at said second wavelength the concentration of the compound of formula (I) in the fuel composition.

14. The composition according claim 4 wherein $R^1$ is hydrogen or an alkyl, alkenyl or alkaryl group having 1 to 12 carbon atoms and each of $R^2$, $R^3$ and $R^4$ is an alkyl, alkenyl or alkaryl group having 1 to 36 carbon atoms, provided that that at least one of $R^2$, $R^3$ and $R^4$ has at least 6 carbon atoms.

15. The composition according claim 4 wherein $R^1$ is hydrogen or an alkyl group having 1 to 4 carbon atoms, $R^2$ is benzyl or an alkyl group having 1 to 4 carbon atoms, and each of $R^3$ and $R^4$ is an alkyl, alkenyl or alkaryl group having 1 to 36 carbon atoms, provided that that at least one of $R^3$ and $R^4$ has at least 6 carbon atoms.

16. The composition according claim 4 wherein $R^1$, $R^2$, $R^3$ and $R^4$ together comprise in total from 16 to 40 carbon atoms, preferably from 20 to 36 carbon atoms, for example from 20 to 30 carbon atoms.

17. The composition according claim 4 wherein each of $R^1$, $R^2$, $R^3$ and $R^4$ is an unsubstituted alkyl or alkenyl group; and each of $R^3$ and $R^4$ has at least 6 carbon atoms.

18. The composition according claim 4 wherein $R^1$ is hydrogen or an unsubstituted alkyl group having 1 to 4 carbon atoms; $R^2$ is an unsubstituted alkyl group having 1 to 4 carbon atoms or an unsubstituted alkyl or alkenyl group having 6 to 36 carbon atoms, preferably 8 to 30 carbon atoms; $R^3$ is benzyl, an unsubstituted alkyl group having 1 to 4 carbon atoms or an unsubstituted alkyl or alkenyl group having 6 to 36 carbon atoms, preferably 8 to 30 carbon atoms; and $R^4$ is an unsubstituted alkyl or alkenyl group having 6 to 36 carbon atoms, preferably 8 to 30 carbon atoms.

19. The composition according claim 4 wherein n is from 1 to 4.

20. The composition according claim 4 wherein the compound of formula (I) has the structure (II):

or an isomer thereof.

21. A kit for determining the concentration of a compound of formula (I) in a fuel composition, the kit comprising means for applying electromagnetic radiation having a first wavelength to said fuel composition; and means for measuring emission of electromagnetic radiation at a second wavelength.

* * * * *